(12) United States Patent
Dobrovolny

(10) Patent No.: US 6,572,540 B2
(45) Date of Patent: Jun. 3, 2003

(54) CAM-WEDGE LOCKING MECHANISM

(75) Inventor: Walter Dobrovolny, St. Paul, MN (US)

(73) Assignee: Minnesota Scientific, Inc., St. Paul, MN (US)

(*) Notice: Subject to any disclaimer, the term of this patent is extended or adjusted under 35 U.S.C. 154(b) by 18 days.

(21) Appl. No.: 09/864,681

(22) Filed: May 24, 2001

(65) Prior Publication Data
US 2002/0177752 A1 Nov. 28, 2002

(51) Int. Cl.$^7$ ................................................ A61B 1/32
(52) U.S. Cl. ............................................... 600/226
(58) Field of Search ................................. 600/201, 210, 600/213, 215, 217, 225–230; 74/567; 292/215, 222, 224, 185, 187

(56) References Cited

U.S. PATENT DOCUMENTS

| | | | | |
|---|---|---|---|---|
| 3,667,793 A | * | 6/1972 | Varrin et al. | 292/207 |
| 3,965,890 A | * | 6/1976 | Gauthier | 403/79 |
| 4,052,980 A | * | 10/1977 | Grams et al. | 600/211 |
| 4,064,873 A | * | 12/1977 | Swenson | 600/215 |
| 4,407,493 A | | 10/1983 | Okolischan | 269/93 |
| 4,467,896 A | | 8/1984 | Sauerwein et al. | 188/69 |
| 4,667,561 A | | 5/1987 | Storey et al. | 84/314 |
| 4,710,077 A | | 12/1987 | Ramunas | 409/232 |
| 5,472,247 A | | 12/1995 | Monson | 292/36 |
| 5,482,417 A | | 1/1996 | Erickson | 411/306 |
| 5,893,831 A | * | 4/1999 | Koros et al. | 600/215 |
| 5,902,233 A | | 5/1999 | Farley et al. | 600/213 |
| 5,976,080 A | * | 11/1999 | Farascioni | 600/201 |
| 6,361,488 B1 | * | 3/2002 | Davison et al. | 600/102 |

FOREIGN PATENT DOCUMENTS

DE 38 34 358 C1 10/1988

* cited by examiner

Primary Examiner—Eduardo C. Robert
Assistant Examiner—Michael B. Priddy
(74) Attorney, Agent, or Firm—Kinney & Lange, P.A.

(57) ABSTRACT

A positioning device allowing rotatable travel in one direction only when an inclined member engages a cammed member. The positioning device includes a rotatable cammed member having a surface defined by a decreasing radius, an inclined member movable between a first position and a second position, and a spring for urging the inclined member into engagement with the cammed member.

19 Claims, 2 Drawing Sheets

CAM-WEDGE LOCKING MECHANISM

BACKGROUND OF THE INVENTION

The present invention relates to a locking mechanism. In particular, the present invention relates to a cam and wedge locking mechanism to selectively position a surgical retractor blade attached to a retractor mounting apparatus.

During many types of surgical procedures it is necessary to use a retractor to hold back tissue proximate a surgical incision. The retractor enables a surgeon to work at and in the surgical incision. Retractors typically include a blade and an arm, such as a shaft, to which the blade is attached. The retractor is generally held in place by attachment to a retractor support apparatus that is positioned over a support surface, such as an operating table. The retractor support apparatus is usually attached to a side rail located along one or more sides of the operating table by a clamping device, such as a fulcrum clamp or a cammed clamp.

Current retractors are not easy to manipulate and position over the surgical incision because the arm is typically a solid inflexible rod. Clamping mechanisms to lock the retractors in a precise location are typically cumbersome and require complex maneuvering that may increase the risk of injury to the patient. Typically, adjustment of the retractor occurs at the clamping device which attaches the retractor to the sides of the operating table. Positioning the retractor at this location remains challenging since the clamping device may be difficult to operate, or be located at a place that may increase the risk of contamination to the patient. Thus, an urgent need presently exists to produce a mechanism that overcomes the challenge of positioning the retractor blade.

BRIEF SUMMARY OF THE INVENTION

The present invention is an automatic locking mechanism for selectively positioning a retractor blade of a retractor apparatus. The invention includes a retractor blade attached to a cam and wedge locking mechanism. The cam and wedge locking mechanism permits rotational movement of the retractor blade from a first position to a second position, but prohibits reverse rotation while the wedge engages the cam. Releasing the wedge from the cam permits rotation of the retractor blade in either direction.

DETAILED DESCRIPTION

Figure 1:
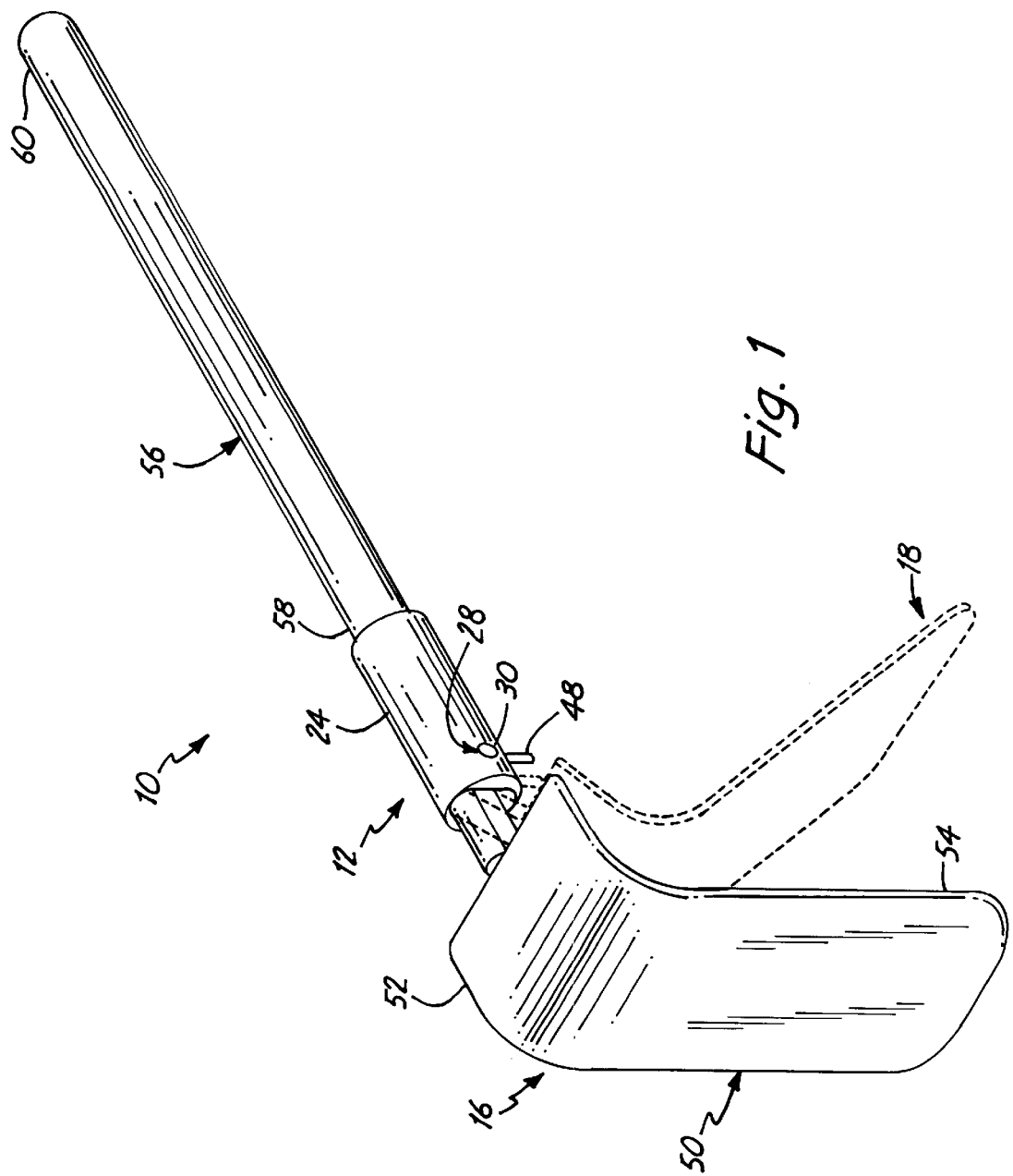
FIG. 1 is a perspective view of the present invention with a retractor blade in a first position (detailed) and a second position (broken lines).

A retractor apparatus suitable for use with the preferred embodiment of the present invention is generally indicated at 10 in FIG. 1. A locking mechanism of the present invention is generally indicated at 12. The locking mechanism 12 is designed to automatically permit rotational movement of a retractor blade 50 in one direction only, from a first upright position 16 to a second downward position 18 (shown in broken lines), while the locking mechanism 12 is engaged. The locking mechanism 12 includes a cammed member 14, a wedge member 20, and a spring 22, all disposed within a housing 24.

The cammed member 14 includes a through-bore 26, the through-bore 26 defining an axis of rotation 27 for the cammed member 14. The housing 24 includes first and second mating apertures 28, only one of which is illustrated. The mating apertures 28 are aligned with each other by being positioned on opposing wall sections. The cammed member 14 is positioned within the housing 24 such that the through-bore 26 aligns with each mating aperture 28.

A securing pin 30 is inserted through the mating apertures 28 and the through-bore 26 of the cammed member 14, thereby rotatably securing the cammed member 14 to the housing 24. Once secured within the housing 24, the cammed member 14 is freely rotatable between the first upright position 16 and the second downward position 18.

Figure 2:
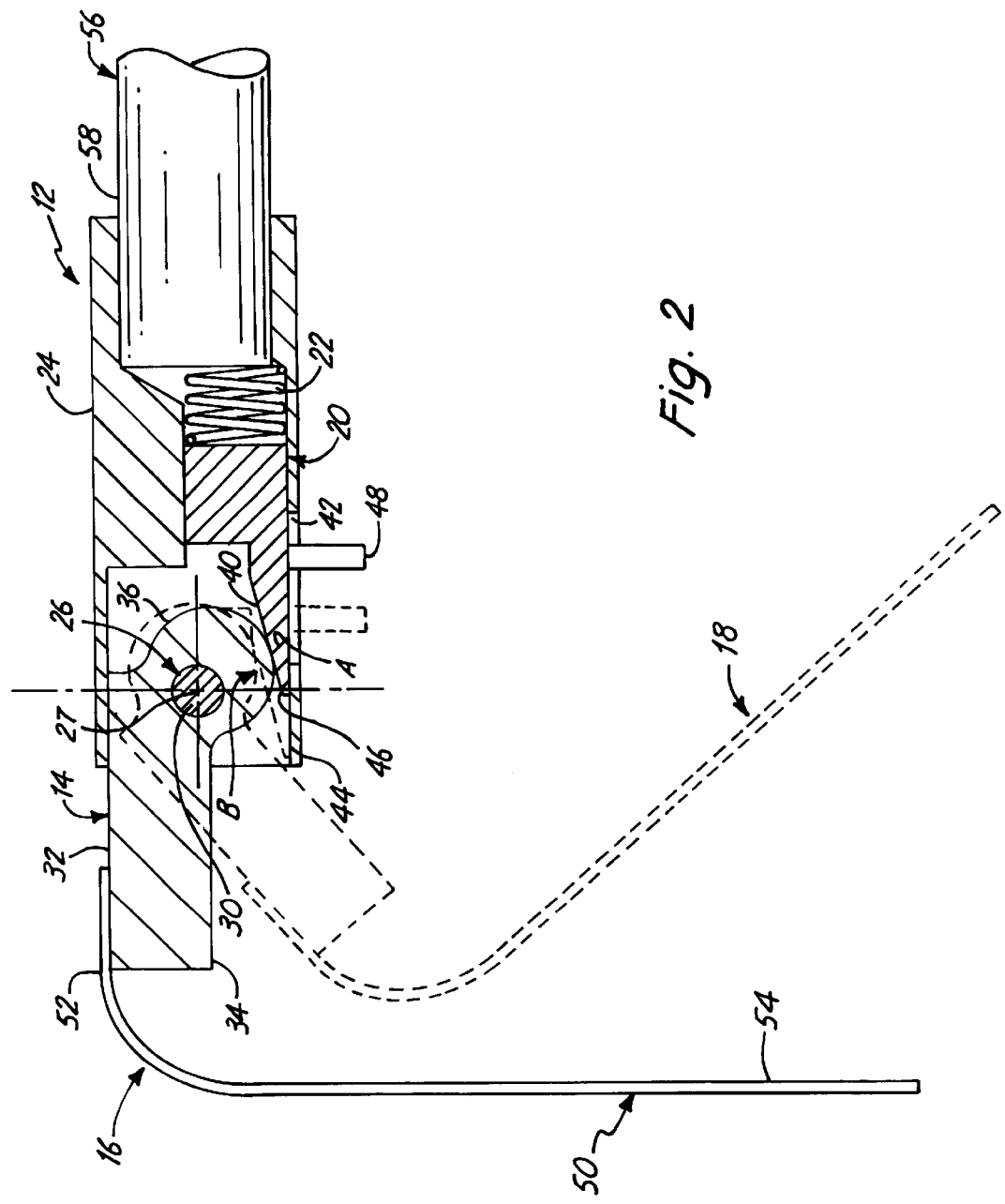
FIG. 2 is a cross-sectional view of the present invention with the retractor blade in a first position (detailed) and a second position (broken lines).

Referring to FIG. 2, the first upright position 16 is defined by a first top side 32 of the cammed member 14 contacting the housing 24, while the second downward position 18 is defined by a second bottom side 34 of the cammed member 14 contacting the housing 24. It should be noted, however, that the terms 'top' and 'bottom' are arbitrary terms, and are used for illustrative purposes with reference to FIG. 2.

The cammed member 14 further includes a cammed surface 36 having a decreasing radius from point A to point B as defined from axis 27. The cammed surface may be the result of an eccentric construction (wherein the axis of rotation is in an offset position) or wherein the cam surface is a lobe offset from the axis of rotation or other construction known in the art. Point A is defined as a point on the cammed surface 36 where an inclined surface 40 of the wedge member 20 contacts the cammed member 14, corresponding to the cammed member 14 in the first upright position 16. Point B is defined as a point on the cammed surface 36 where the inclined surface 40 of the wedge member 20 contacts the cammed member 14, corresponding to the cammed member 14 being in the second downward position 18.

The wedge member 20 is a movable member situated within the housing 24 such that the inclined surface 40 of the wedge member 20 is capable of contacting the cammed surface 36 of the cammed member 14. The wedge member 20 is movable through an infinite number of positions while contacting the wedge member 20. Illustrated in FIG. 2 are a first initial engagement position 42 and a second extended position 44. The first initial engagement position 42 is defined as the position wherein the retractor blade 50 is at a first upright position and the wedge member 20 contacts the cammed member 14. The second extended position 44 is defined as the position wherein the retractor blade 50 is at the second downward position 18 and further forward movement of the wedge member 14 is prohibited. The wedge member is also movable away from the cammed member to a non-engaging position (not shown), wherein the wedge member is disengaged from the cammed member 14, and the retractor blade 50 is freely rotatable in either direction.

A height of the inclined surface 40 of the wedge member 14 is lowest at a first forward end 46 of the wedge member 14, and increases down the length of the wedge member 14, as illustrated in FIG. 2.

The compressible spring 22 urges the wedge member 20 toward the second extended position 44 and against the cammed member 14, thereby contacting the inclined surface 40 of the wedge member 20 with the cammed surface 36 of the cammed member 14. A finger tab 48 is attached to the wedge member 20. The finger tab 48 allows a user to withdraw the wedge member 20 away from contacting the cammed member 14 and toward the first position 42.

In operation, a force is applied to the finger tab 48 which overcomes the force of the compressible spring 22, thereby allowing the wedge member 20 to withdraw away from the cammed member 14 toward and even beyond the first initial engaging position 42. Upon moving past the first non-engaging position, the cammed member 14 is freely rotatable in either direction. The retractor blade 50, and thus the cammed member 14 is manually positionable in the first upright position 16 by engaging the finger tab 48 and urging the wedge member 20 toward the first position 42. Upon removal of the force applied to the finger tab 48, the compression spring 22 urges the wedge member 20 into contact with the cammed member 14. Upon the wedge member 20 engaging the cammed member 14, the cammed member 14 is only rotatable from the first upright position 16 to the second downward position 18, and not in reverse.

As the cammed member 14 rotates from the first position 16 to the second position 18, the decreasing radius from point A to point B of the cammed surface 36 allows the compression spring 22 to urge the wedge member 20 toward the second extended position 44, the wedge member 20 in continuous contact with the cammed member 14. Reverse-rotation of the cammed member 14 in the direction from the second downward position 18 to the first upward position 16 is not possible because the cammed surface 36 of the cammed member 14 will be forced against the inclined surface 40 of the wedge member 20. The relative increase in length of the radius of the cammed member 14, from point B to point A, which defines the cammed surface 36, in conjunction with the increase in height of the wedge member 20, prohibits rotatable travel of the cammed member 14 in the reverse direction.

To rotate the cammed member 14 toward the first upright position 16, a force is applied to the finger tab 48 to overcome the force of the compression spring 22 allowing the wedge member 20 to slide toward the first initial engaging position 42. When the wedge member 20 moves past the initial engaging position 42, the wedge member 20 disengages from the cammed member 14, and the cammed member 14 is freely rotatable in either direction. The cammed member 14 can then be positioned in the first upright position 16.

In the preferred embodiment of the present invention, the retractor blade 50 is attached to the cammed member 14. As illustrated in each figure, the retractor blade 50 has a general "L"-shaped configuration with a first leg 52 attached to the cammed member 14. A second leg 54 of the retractor blade extends past the locking mechanism 12, and is configured to retract flesh, such as skin and muscle tissue, in a selected position during a surgical operation. Preferably, the retractor apparatus 10 includes an arm 56 having a proximate end 58 and a distal end 60. The housing 24 of the retractor apparatus 10 is attached to the proximate end 58 of the arm 56.

In use, the retractor blade 50, which is in the first upright position 16, is positioned within the surgical incision, and the distal end 60 of the arm 56 is secured to the operating table (not shown). The surgeon is then able to further position the retractor blade 50 by rotating retractor blade 50, and thus the cammed member 14, toward the second downward position 18.

When a selected position of the retractor blade 50 is obtained, there being an infinite number of selectable positions between the first upright position 16 and the second downward position 18, the retractor blade 50 is held at the selected position due to the automatic locking mechanism 12. A load on the retractor blade 50, which is provided by the retained flesh, tends to urge the retractor blade 50 in the reverse direction toward the first upright position 16. However, when the wedge member 20 engages the cammed member 14, rotation in the reverse direction is not permitted, and the flesh is retained at the selected position. Thus, the retractor blade 50 is automatically held at the selected position. The retractor blade 50 can be further positioned to increase access to the operable area if the surgeon desires by further rotating the retractor blade 50, and thus the cammed member 14. Any amount of rotation of the cammed member 14 in the direction of the second downward position 18 will lock the cammed member 14 at that position.

To reposition the retractor blade 50 toward the first upright position 16, a force to overcome the compression spring 22 is applied to the finger tab 48 urging the wedge member 20 towards the first initial engaging position 42. As the wedge member 20 travels towards the initial engaging position 42, the relative height of the inclined surface 40 decreases allowing the cammed member 14, which has a tendency to rotate toward the first upright position 16 due to the load bearing on the retractor blade 50, to rotate in the reverse direction because of the relatively increasing radius of the cammed surface 36 contacting the relatively decreasing height of the inclined surface 40 of the wedge member 20. Any movement of the wedge member 20 toward the first non-engaging position will cause the cammed member 14 to reverse rotate and thus affecting the position of the retractor blade 50 towards the first upright position 16.

To remove the retractor apparatus 10 upon completion of the surgical procedure, the finger tab 48 is used to position the wedge member 20 past the initial engaging position 42, thus allowing the cammed member 14 to be freely rotatable. The retractor blade 50 is brought to the first upright position 16, and the apparatus 10 is removed from the surgical site.

Although the present invention has been described with reference to preferred embodiments, workers skilled in the art will recognize that changes may be made in form and detail without departing from the spirit and scope of the invention.

What is claimed is:

1. A positioning mechanism for securing a rotatable member in a selected position, the mechanism preventing reverse-rotation of the rotatable member, the positioning mechanism comprising:

a rotatable cam;

a movable wedge including an inclined surface abuttable against the cam; and a spring for urging the wedge against the cam wherein the cam is rotated and retained in any selected position along the inclined surface of the wedge wherein the wedge prevents reverse-rotation of the cam when engaged with the cam.

2. The positioning mechanism of claim 1 wherein the cam includes a surface defined by a decreasing radius.

3. The positioning mechanism of claim 1 and further comprising:

a finger tab attached to the wedge; and a housing disposed about the wedge, the finger tab extending therethrough.

4. The positioning mechanism of claim 1 and further comprising a surgical retractor blade attached to the cam, the surgical retractor blade movable between a first position and a second position.

5. A positioning device comprising:

a cammed member movable about an axis;

an inclined member movable between a first position and a second position, the inclined member allowing rotatable travel of the cammed member in one direction only when engaging the cammed member; and a spring for urging the inclined member into an engagement with the cammed member wherein the engagement of the cammed member and the inclined member retains the cammed member in any selected position between the first position and the second position on the inclined member.

6. The positioning device of claim 1 wherein the cammed member has a surface defined by a radius of varying lengths.

7. The positioning device of claim 6 and further comprising:

a finger tab attached to the inclined member; and a housing disposed about the inclined member, the finger tab extending through the housing.

8. The positioning device of claim 1 and further comprising a surgical retractor blade, the surgical retractor blade attached to the cammed member.

9. The positioning device of claim 7 wherein the surgical retractor blade is movable between a first position and a second position.

10. The positioning device of claim 5 and further comprising a housing member, the housing member being disposed about the cammed member, the inclined member and the spring.

11. The positioning device of claim 1 wherein the cammed member includes a surface defined by a decreasing radius and the surface being cooperably engageable with the inclined member.

12. An automatically locking retractor apparatus comprising:

a retractor blade;

a cammed member attached to the retractor blade and having a cam defined by a radius of varying lengths; and a wedge capable of engaging the cam surface to retain the cammed member in a fixed position thereby selectively positioning the retractor blade.

13. The automatically locking retractor apparatus of claim 12 and further comprising a spring, the spring urging the wedge into engagement with the cam surface.

14. The automatically locking retractor apparatus of claim 13 and further comprising:

a finger tab attached to the wedge; and a housing disposed about the wedge, the finger tab extending therethrough.

15. The automatically locking retractor apparatus of claim 12 wherein the retractor blade is freely rotatable when the wedge is disengaged from the cam surface.

16. The automatically locking retractor apparatus of claim 12 wherein the wedge is movable between a cam engaging position and a cam non-engaging position.

17. A method of selectively positioning a retractor blade of a retractor apparatus, the apparatus including a cam rotatable about an axis and attached to the retractor blade and a wedge for slidably engaging the cam and a spring force urging the wedge against the cam, the method comprising:

rotating the retractor blade to a selected position; and engaging the retractor blade with body tissue, the cam thereby being engaged by the wedge so that the blade is retained in the selected position.

18. The method of claim 17 and further comprising disengaging the spring force thereby releasing the cam from engagement with the wedge so that the retractor blade may be freely moved to another position.

19. The method of claim 17 wherein the retractor blade is movable in a direction toward the body tissue while immovable in an opposite direction.

* * * * *

UNITED STATES PATENT AND TRADEMARK OFFICE
CERTIFICATE OF CORRECTION

PATENT NO. : 6,572,540 B2
DATED : June 3, 2003
INVENTOR(S) : Walter Dobrovolny

It is certified that error appears in the above-identified patent and that said Letters Patent is hereby corrected as shown below:

Column 5,
Lines 9 and 16, delete "1" and insert -- 5 --.
Line 19, delete "7" and insert -- 3 --.
Lines 19-20, delete "the surgical retractor".
Line 26, delete "1" and insert -- 5 --.

Signed and Sealed this

Twenty-seventh Day of July, 2004

JON W. DUDAS
*Acting Director of the United States Patent and Trademark Office*